United States Patent [19]
Bandman et al.

[11] Patent Number: 5,786,148
[45] Date of Patent: Jul. 28, 1998

[54] POLYNUCLEOTIDES ENCODING A NOVEL PROSTATE-SPECIFIC KALLIKREIN

[75] Inventors: Olga Bandman, Mountain View; Surya K. Goli, Sunnyvale, both of Calif.

[73] Assignee: Incyte Pharmaceuticals, Inc., Palo Alto, Calif.

[21] Appl. No.: 744,026

[22] Filed: Nov. 5, 1996

[51] Int. Cl.$^6$ .............................. C12P 21/02; C12Q 1/68; C07H 21/04; C12N 15/63

[52] U.S. Cl. .................... 435/6; 435/252.3; 435/320.1; 435/212; 536/23.2; 536/24.31

[58] Field of Search ...................... 435/212, 320.1, 435/252.3, 6; 536/23.2, 24.31

[56] References Cited

PUBLICATIONS

Bridon, D.P. et al., "Structural comparison of Prostate–Specific Antigen and Human Glandular Kallikrein Using Molecular Modeling" *Urology* 45:801–806 (1995).

Christensson, A. et al., "Enzymatic activity of prostate–specific antigen and its reactions with extracellular serine proteinase inhibitors" *Eur. J. Biochem* 194:755–763 (1990).

Cramer S.D. et al., "Prostate specific antigen cleaves parathyroid hormone–related protein in the PTH–like domain: inactivation of PTHrP–stimulated cAMP accumulation in mouse osteoblasts" *J. Urol.* 156:526–531 (1996).

Evans B.A. et al., "Structure and chromosomal localizaiton of the human renal kallikrein gene" *Biochemistry* 27:3124–3129 (1988) (Accession GI 186651).

Fukushima, D. et al., "Nucleotide sequence of cloned cDNA for human pancreatic kallikrein" *Biochemistry* 24:8037–8043 (1985).

Henttu P. et al., "Prostate–specific antigen and human glandular kallikrein: two kallikreins of the human prostate" *Ann. Med.* 26:157–164 (1994).

Lundwall, A., "Characterization of the gene for prostate–specific antigen, a human glandular kallikrein" *Biochem Biophys Res Commun* 161:1151–1159 (1989) (Accession GI 190553).

Perelygina, et al., (Direct Submission), GenBank Sequence Database Accession GI 871814), National Center for Biotechnology Information, National Library of Medicine, Bethesda, Maryland 20894 (1995).

Riegman, P.H. et al., "Characterization of the human kallikrein locus" *Genomics* 14:6–11 (1992).

*Primary Examiner*—Robert A. Wax
*Assistant Examiner*—Kawai Lau
*Attorney, Agent, or Firm*—Lucy J. Billings

[57] ABSTRACT

The present invention provides a human prostate-specific kallikrein (HPSK) and polynucleotides which identify and encode HPSK. The invention also provides genetically engineered expression vectors and host cells comprising the nucleic acid sequences encoding HPSK and a method for producing HPSK. The invention also provides for agonists, antibodies, or antagonists specifically binding HPSK, and their use, in the prevention and treatment of diseases associated with expression of HPSK. Additionally, the invention provides for the use of antisense molecules to polynucleotides encoding HPSK for the treatment of diseases associated with the expression of HPSK. The invention also provides diagnostic assays which utilize the polynucleotide, or fragments or the complement thereof, and antibodies specifically binding HPSK.

11 Claims, 8 Drawing Sheets

```
                                  9                18               27               36               45              54
5' ACC TGC TGG CCC CTG GAC ACC TCT GTC ACC ATG TGG TTC CTG TGC CTC
                                                          M   W   F   L   C   L 63               72               81               90               99              108
   GCC CTG TCC CTG GGG ACT GGT GCT GCG CCC ATT CAG CCC ATT TCC CGG ATT GTG
    A   L   S   L   G   T   G   A   A   P   I   Q   P   I   S   R   I   V 117              126              135              144              153              162
   GGA GGC TGG GAG TGT GAG CAG CAT TCC CAG CCC TGG CAG GCG CTG GTC ATG
    G   G   W   E   C   E   Q   H   S   Q   P   W   Q   A   L   V   M 171              180              189              198              207              216
   GAA AAC GAA TTG TTC TGC TCG GGC GTC CTG GTG CAT CCG CAG TGG GTG CTG TCA
    E   N   E   L   F   C   S   G   V   L   V   H   P   Q   W   V   L   S 225              234              243              252              261              270
   GCC GCA CAC TGT TTC CAG AAC TCC TAC ACC ATC GGG CTG GGC CTG CAC AGT CTT
    A   A   H   C   F   Q   N   S   Y   T   I   G   L   G   L   H   S   L 279              288              297              306              315              324
   GAG GCC GAC CAA GAG CCA GGG AGC CAG ATG GTG GAG GCC AGC CTC TCC GTA CGG
    E   A   D   Q   E   P   G   S   Q   M   V   E   A   S   L   S   V   R 333              342              351              360              369              378
   CAC CCA GAG TAC AAC AGA CCC TTG CTC GCT AAC GAC CTC ATG NTC ATC AAG TTG
    H   P   E   Y   N   R   P   L   L   A   N   D   L   M   X   I   K   L
```

FIGURE 1A

```
GAC GAA TCC GTG TCC GAG TCT GAC AAC ATC CGG AGN ATC AGC ATT GNT TCG CAG
 D   E   S   V   S   E   S   D   N   I   R   X   I   S   I   X   S   Q
387         396         405         414         423         432

TGC CCT ACC GCG GGG AAC TTT TGC CTC GTT TCT GGC TGG GGT CTG CTG GCG AAC
 C   P   T   A   G   N   F   C   L   V   S   G   W   G   L   L   A   N
441         450         459         468         477         486

GGC AGA ATG CCT ACC GTG CTG CAG GTG CTG AAC TCG GTG TCT GAG GAG
 G   R   M   P   T   V   L   Q   V   L   N   S   V   S   E   E
495         504         513         522         531         540

GTC TGC AGT AAG CTC TAT GAC CCG TAC CAC CCC AGC ATG TTC TGC GCC GGC
 V   C   S   K   L   Y   D   P   Y   H   P   S   M   F   C   A   G
549         558         567         576         585         594

GGA GGG CAA GAC CAG GGC CTT GTG TCC AAC GGT GAC TCT GGG GGG CCC CTG ATC
 G   G   Q   D   Q   G   L   V   S   N   G   D   S   G   G   P   L   I
603         612         621         630         639         648

TGC AAC GGG TAC TTG CAG GGC CTT GTG TCT TTC GGA AAA GCC CCG TGT GGC CAA
 C   N   G   Y   L   Q   G   L   V   S   F   G   K   A   P   C   G   Q
657         666         675         684         693         702

GTT GGC GTC CCA GGT GTC TAC ACC AAC CTC TGC AAA TTC ACT GAG TGG ATA GAG
 V   G   V   P   G   V   Y   T   N   L   C   K   F   T   E   W   I   E
711         720         729         738         747         756
```

FIGURE 1B

```
                765                774            783           792          801          810
AAA ACC GTC CAG GCC AGT TAA CTC TGG GGA CTG GGA ACC CAT GAA ATT GAC CCC
 K   T   V   Q   A   S
                819            828            837            846            855           864
CAA ATA CAT CCT GCG GAA GGA ATT CAG GAA TAT CTG TTC CCA GCC CCT CCT CCC

TCA GGC C 3'
```

FIGURE 1C

```
  1  M W F L V L C L A L S L G G T G A A P P I Q S R I V G G W E C E Q H S Q P W Q A   SEQ ID NO-1
  1  M W F L V L C L A L S L G G T G A A P P I Q S R I V G G W E C E Q H S Q P W Q A A L Y   GI 871814
  1  M W F L V L C L A L S L G G T G A A P P I Q S R I V G G W E C E Q H S Q P W Q A   GI 186651
  1  M W V P V V F L T L S V T W I G A A P L I L S R I V G G W E C E K H S Q P W Q V   GI 190553

41  A L V M E N E L F C S G V L V H P Q W V L S A A H C F Q N S Y T I G L G L H S L   SEQ ID NO-1
 41  H F S T F Q C G G I L V H P Q W V L T A A H C I G D N Y Q L W L G R H N L F D D   GI 871814
 41  A L Y H F S T F Q C G G I L V H R Q W V L T A A H C I S D N Y Q L W L G R H N L   GI 186651
 41  L V A S R G R A V C G G V L V H P Q W V L T A A H C I R N K S V I L L G R H S L   GI 190553

81  E A D Q E P G S Q M V E A S L S V R H P E Y N R P L L A N D L M X I K L D E S V   SEQ ID NO-1
 81  E D T A Q F V H V S E S F P H P C F N M S L L K N H T R Q A D E D Y S H D L M L   GI 871814
 81  F D D E N T A Q F V H V S E S F P H P G F N M S L L E N H T R Q A D E D Y S H D   GI 186651
 81  F H P E D T G Q V F Q V S H S F P H P L Y D M S L L K N R F L R P G D D S S H D   GI 190553

121  S E S D N I R X I S I X S Q C P T A G N F C L V S G W G L L A N G R M P T V L Q   SEQ ID NO-1
121  L R L T Q P A E I T D A V Q V V E L P T Q E P E V G S T C L A S G W G S I E P E   GI 871814
121  L M L L R L T E P A D T I T D A V K V V E L P T Q E P E V G S T C L A S G W G S   GI 186651
121  L M L L R L S E P A E L T D A V K V M D L P T Q E P A L G T T C Y A S G W G S I   GI 190553

161  C V N V S V V S E E V C S K L Y D P L Y H P S M F C A G G G D Q K D S C N G D   SEQ ID NO-1
161  N F S Y P D D L Q C V D L K I L P N D K C A K A H T Q K V T E F M L C A G H L E   GI 871814
161  I E P E N F S F P D D L Q C V D L K I L P N D E C K K A H V Q K V T D F M L C V   GI 186651
161  E P E E F L T P K K L Q C V D L H V I S N D V C A Q V H P Q K V T K F M L C A G   GI 190553
```

FIGURE 2A

```
201 S G G P L I C N G Y L Q G L V S F G K A P C G Q V G V P G V Y T N L C K F T E W   SEQ ID NO-1
201 G G K D T C V G D S G G P L T C D G V L Q G V T S W G Y I P C G S P N K P A V F   GI 871814
201 G H L E G G K D T C V G D S G G P L M C D G V L Q G V T S W G Y V P C G T P N K   GI 186651
201 R W T G G K S T C S G D S G G P L V C N G V L Q G I T S W G S E P C A L P E R P   GI 190553

241 I E K T V Q A S                                                                   SEQ ID NO-1
241 V R V L S Y V K W I E D T I A E N S                                               GI 871814
241 P S V A V R V L S Y V K W I E D T I A E N S                                       GI 186651
241 S L Y T K V V H Y R K W I K D T I V A N P                                         GI 190553
```

FIGURE 2B

| Library | Lib Description | Abun | Pct Abun |
|---|---|---|---|
| PROSTUT12 | prostate tumor, 65 M, match to PROSNOT20 | 9 | 0.2515 |
| PROSNOT20 | prostate, 65 M, match to PROSTUT12 | 5 | 0.1678 |
| PROSNOT02 | prostate, 50 M, match to PROSTUT01 | 3 | 0.1304 |
| PROSTUT05 | prostate tumor, 69 M, match to PROSNOT07 | 6 | 0.0870 |
| PROSTUT08 | prostate tumor, 60 M, match to PROSNOT14 | 1 | 0.0532 |
| PROSNOT14 | prostate, 60 M, match to PROSTUT08 | 2 | 0.0512 |
| PROSNOT15 | prostate, 66 M, match to PROSTUT10 | 2 | 0.0483 |
| PROSNOT11 | prostate, 28 M | 1 | 0.0282 |
| PROSNOT19 | prostate, 59 M | 1 | 0.0272 |
| PROSTUT10 | prostate tumor, 66 M, match to PROSNOT15 | 1 | 0.0268 |
| PROSTUT04 | prostate tumor, 57 M, match to PROSNOT06 | 2 | 0.0234 |
| PROSNOT06 | prostate, 57 M, match to PROSTUT04 | 2 | 0.0228 |
| BRSTNOT04 | breast, 62 F | 1 | 0.0096 |

FIGURE 5

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 248 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY:

(B) CLONE: Consensus (xi) SEQUENCE DESCRIPTION: SEQ ID NO:1:

| Met | Trp | Phe | Leu | Val | Leu | Cys | Leu | Ala | Leu | Ser | Leu | Gly | Gly | Thr | Gly |
| 1 | | | | 5 | | | | | 10 | | | | | 15 | |
| Ala | Ala | Pro | Pro | Ile | Gln | Ser | Arg | Ile | Val | Gly | Gly | Trp | Glu | Cys | Glu |
| | | | 20 | | | | | 25 | | | | | 30 | | |
| Gln | His | Ser | Gln | Pro | Trp | Gln | Ala | Ala | Leu | Val | Met | Glu | Asn | Glu | Leu |
| | | | 35 | | | | | 40 | | | | | 45 | | |
| Phe | Cys | Ser | Gly | Val | Leu | Val | His | Pro | Gln | Trp | Val | Leu | Ser | Ala | Ala |
| | | 50 | | | | | 55 | | | | | 60 | | | |
| His | Cys | Phe | Gln | Asn | Ser | Tyr | Thr | Ile | Gly | Leu | Gly | Leu | His | Ser | Leu |
| 65 | | | | | 70 | | | | | 75 | | | | | 80 |
| Glu | Ala | Asp | Gln | Glu | Pro | Gly | Ser | Gln | Met | Val | Glu | Ala | Ser | Leu | Ser |
| | | | | 85 | | | | | 90 | | | | | 95 | |
| Val | Arg | His | Pro | Glu | Tyr | Asn | Arg | Pro | Leu | Leu | Ala | Asn | Asp | Leu | Met |
| | | | | 100 | | | | | 105 | | | | | 110 | |
| Xaa | Ile | Lys | Leu | Asp | Glu | Ser | Val | Ser | Glu | Ser | Asp | Asn | Ile | Arg | Xaa |
| | | | 115 | | | | | 120 | | | | | 125 | | |
| Ile | Ser | Ile | Xaa | Ser | Gln | Cys | Pro | Thr | Ala | Gly | Asn | Phe | Cys | Leu | Val |
| | | 130 | | | | | 135 | | | | | 140 | | | |
| Ser | Gly | Trp | Gly | Leu | Leu | Ala | Asn | Gly | Arg | Met | Pro | Thr | Val | Leu | Gln |
| 145 | | | | | 150 | | | | | 155 | | | | | 160 |
| Cys | Val | Asn | Val | Ser | Val | Val | Ser | Glu | Glu | Val | Cys | Ser | Lys | Leu | Tyr |
| | | | | 165 | | | | | 170 | | | | | 175 | |
| Asp | Pro | Leu | Tyr | His | Pro | Ser | Met | Phe | Cys | Ala | Gly | Gly | Gly | Gln | Asp |
| | | | 180 | | | | | 185 | | | | | 190 | | |
| Gln | Lys | Asp | Ser | Cys | Asn | Gly | Asp | Ser | Gly | Gly | Pro | Leu | Ile | Cys | Asn |
| | | | 195 | | | | | 200 | | | | | 205 | | |
| Gly | Tyr | Leu | Gln | Gly | Leu | Val | Ser | Phe | Gly | Lys | Ala | Pro | Cys | Gly | Gln |
| | | | 210 | | | | | 215 | | | | | 220 | | |
| Val | Gly | Val | Pro | Gly | Val | Tyr | Thr | Asn | Leu | Cys | Lys | Phe | Thr | Glu | Trp |
| 225 | | | | | 230 | | | | | 235 | | | | | 240 |
| Ile | Glu | Lys | Thr | Val | Gln | Ala | Ser |
| | | | | 245 | | | |

(2) INFORMATION FOR SEQ ID NO:2:

(i) SEQUENCE CHARACTERISTICS:
(A) LENGTH: 871 base pairs
(B) TYPE: nucleic acid
(C) STRANDEDNESS: single
(D) TOPOLOGY: linear (vii) IMMEDIATE SOURCE:
(A) LIBRARY:
(B) CLONE: Consensus (xi) SEQUENCE DESCRIPTION: SEQ ID NO:2:

```
ACCTGCTGGC CCCTGGACAC CTCTGTCACC ATGTGGTTCC TGGTTCTGTG CCTCGCCCTG      60
TCCCTGGGGG GGACTGGTGC TGCGCCCCCG ATTCAGTCCC GGATTGTGGG AGGCTGGGAG     120
TGTGAGCAGC ATTCCCAGCC CTGGCAGGCG GCACTGGTCA TGGAAAACGA ATTGTTCTGC     180
TCGGGCGTCC TGGTGCATCC GCAGTGGGTG CTGTCAGCCG CACACTGTTT CCAGAACTCC     240
TACACCATCG GGCTGGGCCT GCACAGTCTT GAGGCCGACC AAGAGCCAGG GAGCCAGATG     300
GTGGAGGCCA GCCTCTCCGT ACGGCACCCA GAGTACAACA GACCCTTGCT CGCTAACGAC     360
CTCATGNTCA TCAAGTTGGA CGAATCCGTG TCCGAGTCTG ACAACATCCG GAGNATCAGC     420
```

```
ATTGNTTCGC  AGTGCCCTAC  CGCGGGGAAC  TTTTGCCTCG  TTTCTGGCTG  GGGTCTGCTG      480

GCGAACGGCA  GAATGCCTAC  CGTGCTGCAG  TGCGTGAACG  TGTCGGTGGT  GTCTGAGGAG      540

GTCTGCAGTA  AGCTCTATGA  CCCGCTGTAC  CACCCCAGCA  TGTTCTGCGC  CGGCGGAGGG      600

CAAGACCAGA  AGGACTCCTG  CAACGGTGAC  TCTGGGGGGC  CCCTGATCTG  CAACGGGTAC      660

TTGCAGGGCC  TTGTGTCTTT  CGGAAAAGCC  CCGTGTGGCC  AAGTTGGCGT  GCCAGGTGTC      720

TACACCAACC  TCTGCAAATT  CACTGAGTGG  ATAGAGAAAA  CCGTCCAGGC  CAGTTAACTC      780

TGGGGACTGG  GAACCCATGA  AATTGACCCC  CAAATACATC  CTGCGGAAGG  AATTCAGGAA      840

TATCTGTTCC  CAGCCCCTCC  TCCCTCAGGC  C                                      871
```

( 2 ) INFORMATION FOR SEQ ID NO:3:

( i ) SEQUENCE CHARACTERISTICS:
        ( A ) LENGTH: 258 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 871814

( x i ) SEQUENCE DESCRIPTION: SEQ ID NO:3:

```
Met  Trp  Phe  Leu  Val  Leu  Cys  Leu  Ala  Leu  Ser  Leu  Gly  Gly  Thr  Gly
 1              5                        10                       15

Ala  Ala  Pro  Pro  Ile  Gln  Ser  Arg  Ile  Val  Gly  Gly  Trp  Glu  Cys  Ser
               20                       25                       30

Gln  Pro  Trp  Gln  Ala  Ala  Leu  Tyr  His  Phe  Ser  Thr  Phe  Gln  Cys  Gly
                35                       40                       45

Gly  Ile  Leu  Val  His  Pro  Gln  Trp  Val  Leu  Thr  Ala  Ala  His  Cys  Ile
          50                       55                       60

Gly  Asp  Asn  Tyr  Gln  Leu  Trp  Leu  Gly  Arg  His  Asn  Leu  Phe  Asp  Asp
 65                      70                       75                       80

Glu  Asp  Thr  Ala  Gln  Phe  Val  His  Val  Ser  Glu  Ser  Phe  Pro  His  Pro
                    85                       90                       95

Cys  Phe  Asn  Met  Ser  Leu  Leu  Lys  Asn  His  Thr  Arg  Gln  Ala  Asp  Glu
                100                      105                      110

Asp  Tyr  Ser  His  Asp  Leu  Met  Leu  Leu  Arg  Leu  Thr  Gln  Pro  Ala  Glu
               115                      120                      125

Ile  Thr  Asp  Ala  Val  Gln  Val  Val  Glu  Leu  Pro  Thr  Gln  Glu  Pro  Glu
          130                      135                      140

Val  Gly  Ser  Thr  Cys  Leu  Ala  Ser  Gly  Trp  Gly  Ser  Ile  Glu  Pro  Glu
145                      150                      155                      160

Asn  Phe  Ser  Tyr  Pro  Asp  Asp  Leu  Gln  Cys  Val  Asp  Leu  Lys  Ile  Leu
                    165                      170                      175

Pro  Asn  Asp  Lys  Cys  Ala  Lys  Ala  His  Thr  Gln  Lys  Val  Thr  Glu  Phe
               180                      185                      190

Met  Leu  Cys  Ala  Gly  His  Leu  Glu  Gly  Gly  Lys  Asp  Thr  Cys  Val  Gly
          195                      200                      205

Asp  Ser  Gly  Gly  Pro  Leu  Thr  Cys  Asp  Gly  Val  Leu  Gln  Gly  Val  Thr
     210                      215                      220

Ser  Trp  Gly  Tyr  Ile  Pro  Cys  Gly  Ser  Pro  Asn  Lys  Pro  Ala  Val  Phe
225                      230                      235                      240

Val  Arg  Val  Leu  Ser  Tyr  Val  Lys  Trp  Ile  Glu  Asp  Thr  Ile  Ala  Glu
                    245                      250                      255
```

Asn Ser (2) INFORMATION FOR SEQ ID NO:4:

(i) SEQUENCE CHARACTERISTICS:
(A) LENGTH: 262 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 186651

(xi) SEQUENCE DESCRIPTION: SEQ ID NO:4:

```
Met Trp Phe Leu Val Leu Cys Leu Ala Leu Ser Leu Gly Gly Thr Gly
  1           5                  10                 15
Ala Ala Pro Pro Ile Gln Ser Arg Ile Val Gly Gly Trp Glu Cys Glu
            20                  25                 30
Gln His Ser Gln Pro Trp Gln Ala Ala Leu Tyr His Phe Ser Thr Phe
        35                  40                 45
Gln Cys Gly Gly Ile Leu Val His Arg Gln Trp Val Leu Thr Ala Ala
    50                  55                 60
His Cys Ile Ser Asp Asn Tyr Gln Leu Trp Leu Gly Arg His Asn Leu
 65                 70                 75                     80
Phe Asp Asp Glu Asn Thr Ala Gln Phe Val His Val Ser Glu Ser Phe
                85                  90                 95
Pro His Pro Gly Phe Asn Met Ser Leu Leu Glu Asn His Thr Arg Gln
            100                 105                110
Ala Asp Glu Asp Tyr Ser His Asp Leu Met Leu Leu Arg Leu Thr Glu
            115                 120                125
Pro Ala Asp Thr Ile Thr Asp Ala Val Lys Val Val Glu Leu Pro Thr
        130                 135                140
Gln Glu Pro Glu Val Gly Ser Thr Cys Leu Ala Ser Gly Trp Gly Ser
145                 150                 155                160
Ile Glu Pro Glu Asn Phe Ser Phe Pro Asp Asp Leu Gln Cys Val Asp
                165                 170                175
Leu Lys Ile Leu Pro Asn Asp Glu Cys Lys Lys Ala His Val Gln Lys
            180                 185                190
Val Thr Asp Phe Met Leu Cys Val Gly His Leu Glu Gly Gly Lys Asp
        195                 200                205
Thr Cys Val Gly Asp Ser Gly Gly Pro Leu Met Cys Asp Gly Val Leu
    210                 215                 220
Gln Gly Val Thr Ser Trp Gly Tyr Val Pro Cys Gly Thr Pro Asn Lys
225                 230                 235                240
Pro Ser Val Ala Val Arg Val Leu Ser Tyr Val Lys Trp Ile Glu Asp
                245                 250                255
Thr Ile Ala Glu Asn Ser
            260
```

(2) INFORMATION FOR SEQ ID NO:5:

(i) SEQUENCE CHARACTERISTICS:
(A) LENGTH: 261 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 190553

(xi) SEQUENCE DESCRIPTION: SEQ ID NO:5:

```
Met Trp Val Pro Val Val Phe Leu Thr Leu Ser Val Thr Trp Ile Gly
 1               5                   10                  15
Ala Ala Pro Leu Ile Leu Ser Arg Ile Val Gly Gly Trp Glu Cys Glu
            20                  25                  30
Lys His Ser Gln Pro Trp Gln Val Leu Val Ala Ser Arg Gly Arg Ala
        35              40                      45
Val Cys Gly Gly Val Leu Val His Pro Gln Trp Val Leu Thr Ala Ala
    50              55                      60
His Cys Ile Arg Asn Lys Ser Val Ile Leu Leu Gly Arg His Ser Leu
65                  70                  75                  80
Phe His Pro Glu Asp Thr Gly Gln Val Phe Gln Val Ser His Ser Phe
            85                      90                  95
Pro His Pro Leu Tyr Asp Met Ser Leu Leu Lys Asn Arg Phe Leu Arg
            100                     105                 110
Pro Gly Asp Asp Ser Ser His Asp Leu Met Leu Leu Arg Leu Ser Glu
        115             120                     125
Pro Ala Glu Leu Thr Asp Ala Val Lys Val Met Asp Leu Pro Thr Gln
    130                 135                 140
Glu Pro Ala Leu Gly Thr Thr Cys Tyr Ala Ser Gly Trp Gly Ser Ile
145                 150                     155                 160
Glu Pro Glu Glu Phe Leu Thr Pro Lys Lys Leu Gln Cys Val Asp Leu
                165                 170                     175
His Val Ile Ser Asn Asp Val Cys Ala Gln Val His Pro Gln Lys Val
            180                 185                 190
Thr Lys Phe Met Leu Cys Ala Gly Arg Trp Thr Gly Gly Lys Ser Thr
        195                 200                 205
Cys Ser Gly Asp Ser Gly Gly Pro Leu Val Cys Asn Gly Val Leu Gln
    210                 215                 220
Gly Ile Thr Ser Trp Gly Ser Glu Pro Cys Ala Leu Pro Glu Arg Pro
225                 230                 235                 240
Ser Leu Tyr Thr Lys Val Val His Tyr Arg Lys Trp Ile Lys Asp Thr
            245                 250                 255
Ile Val Ala Asn Pro
            260
```

POLYNUCLEOTIDES ENCODING A NOVEL PROSTATE-SPECIFIC KALLIKREIN

FIELD OF THE INVENTION

This invention relates to nucleic acid and amino acid sequences of a novel prostate-specific kallikrein and to the use of these sequences in the diagnosis, prevention, and treatment of disorders of the prostate, including cancer and benign hyperplasia.

BACKGROUND OF THE INVENTION

Prostate-specific antigen (PSA) is a 33 kD glycoprotein synthesized in the epithelial cells of the prostate gland. It is an secreted serine protease of the kallikrein family. PSA has been shown to digest the seminal vesicle protein, semenogelin, parathyroid hormone-related protein, and insulin-like growth factor-binding protein-3 (Henttu P. et al. (1994) Ann. Med. 26: 157–164; Cramer S. D. et al. (1996) J. Urol. 156: 526–531). PSA is likely to act in semen production, but may have additional functions.

Genes encoding the three human kallikreins, tissue kallikrein (KLK1), glandular kallikrein (KLK2), and APS are located in a cluster at chromosome map position 19q13.2–q13.4 (Riegmen P. H. (1992) Genomics 14: 6–11). PSA shares more extensive homology with KLK2 than with KLK1. Both PSA and KLK2 are produced by prostate epithelial cells and their expression is regulated by androgens. Three amino acid residues were found to be critical for serine protease activity, residues $H_{65}$, $D_{120}$, and $S_{213}$ in PSA (Bridon D. P. et al. (1995) Urology 45: 801–806). Substrate specificity, described as chymotrypsinogen-like (with KLK2) or trypsin-like (with PSA) is thought to be determined by $S_{207}$ in PSA and $D_{209}$ in KLK2 (Bridon et al., supra). KLK1 is chymotrypsinogen-like and expressed in the pancreas, urinary system, and sublingual gland. KLK1, like the other kallikreins, is made as a pre-pro-protein and is processed into an active form of 238 amino acids by cleavage of a 24 amino acid terminal signal sequence (Fukushima D. et al. (1985) Biochemistry 24: 8037–8043).

Adenocarcinoma of the prostate accounts for a significant number of malignancies in men over 50. There are over 122,000 new cases per year in the United States. Prostate-specific antigen (PSA) is the most sensitive marker available for monitoring cancer progression and response to therapy. Serum PSA is elevated in 25 to 92% of patients with prostatic carcinoma, depending upon tumor volume. Since PSA is also moderately elevated in patients with benign prostate hyperplasia, additional techniques are needed to distinguish between the two.

The discovery of polynucleotides encoding additional prostate specific molecules, and the molecules themselves, presents the opportunity to investigate disorders of the prostate, including benign hyperplasia and prostatic carcinoma. Discovery of molecules related to PSA satisfies a need in the art by providing new compositions useful in diagnosis, treatment, and prognosis of prostate cancer and hyperplasia.

SUMMARY OF THE INVENTION

The present invention features a novel prostate-specific kallikrein hereinafter designated HPSK and characterized as having chemical and structural similarity to KLK1.

Accordingly, the invention features a substantially purified HPSK which has the amino acid sequence shown in SEQ ID NO:1.

One aspect of the invention features isolated and substantially purified polynucleotides that encode HPSK. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HPSK. The present invention also features antibodies which bind specifically to HPSK, and pharmaceutical compositions comprising substantially purified HPSK. The invention also features the use of agonists and antagonists of HPSK.

BRIEF DESCRIPTION OF THE FIGURES

FIG. 1 shows the amino acid sequence (SEQ ID NO:1) and nucleic acid sequence (SEQ ID NO:2) of HPSK. The alignment was produced using MacDNASIS PRO™ software (Hitachi Software Engineering Co., Ltd., San Bruno, Calif.).

FIG. 2 shows the amino acid sequence alignments among HPSK (SEQ ID NO:1), baboon KLK1 (GI 871814; SEQ ID NO:3), human KLK1 (GI 186651; SEQ ID NO:4) and human PSA (GI 190553; SEQ ID NO:5). The alignment was produced using the multisequence alignment program of DNASTAR™ software (DNASTAR Inc, Madison Wis.).

FIG. 5 shows the northern analysis for SEQ ID NO:2. The northern analysis was produced electronically using LIFESEQ™ database (Incyte Pharmaceuticals, Inc., Palo Alto, Calif.).

DESCRIPTION OF THE INVENTION

Figure 3:
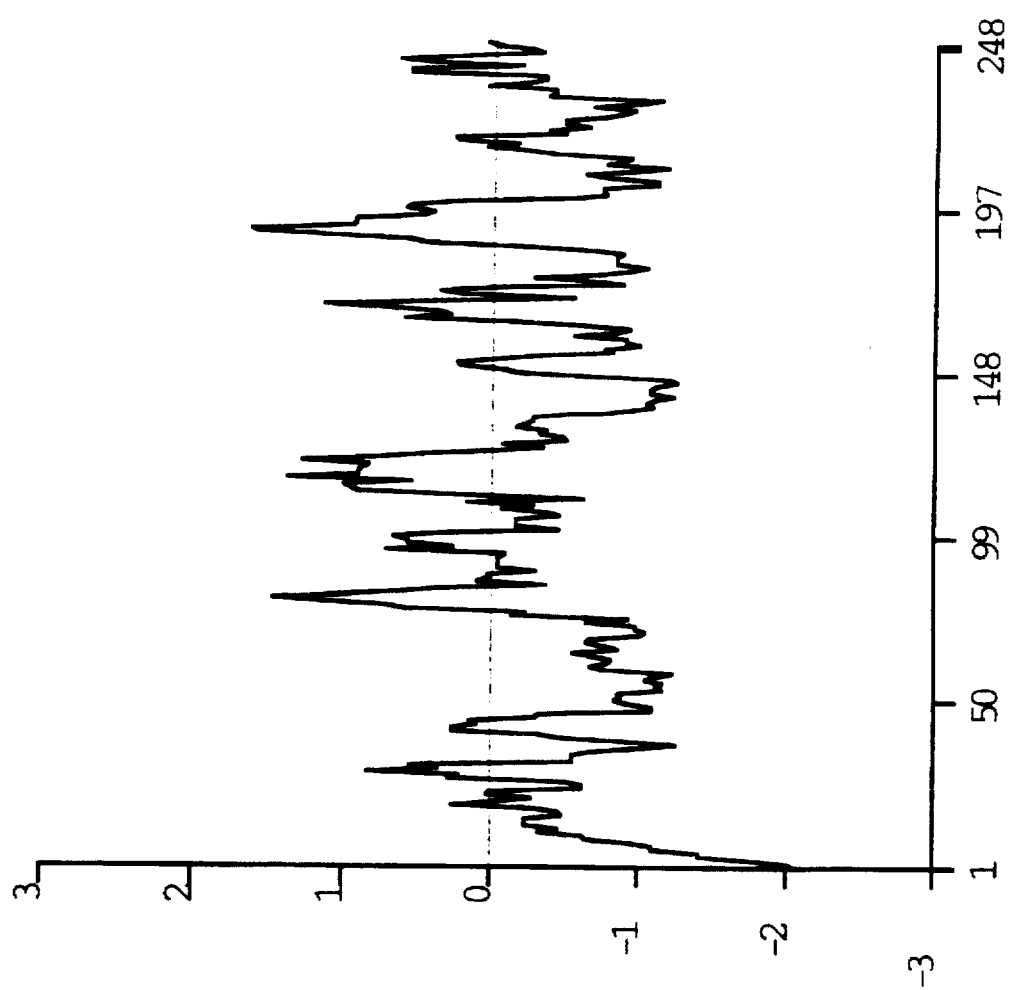
FIG. 3 shows the hydrophobicity plot (MacDNASIS PRO software) for HPSK, SEQ ID NO: 1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8: 53–63).

HPSK, as used herein, refers to the amino acid sequences of substantially purified HPSK obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of HPSK, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HPSK, or any oligopeptide thereof, to induce a specific immune response in appropriate animals or cells and to bind with specific antibodies.

The term "agonist", as used herein, refers to a molecule which, when bound to HPSK, causes a change in HPSK which modulates the activity of HPSK. Agonists may include proteins, nucleic acids, carbohydrates, or any other molecules which bind to HPSK.

The terms "antagonist" or "inhibitor", as used herein, refer to a molecule which, when bound to HPSK, blocks or modulates the biological or immunological activity of HPSK. Antagonists and inhibitors may include proteins, nucleic acids, carbohydrates, or any other molecules which bind to HPSK.

The term "modulate", as used herein, refers to a change or an alteration in the biological activity of HPSK. Modulation may be an increase or a decrease in protein activity, a change in binding characteristics, or any other change in the biological, functional or immunological properties of HPSK.

The term "mimetic", as used herein, refers to a molecule, the structure of which is developed from knowledge of the structure of HPSK or portions thereof and, as such, is able to effect some or all of the actions of KLK1-like molecules.

The term "derivative", as used herein, refers to the chemical modification of a nucleic acid encoding HPSK or the encoded HPSK. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HPSK and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HPSK or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HPSK in a sample and thereby correlates with expression of the transcript from the polynucleotide encoding the protein.

"Alterations" in the polynucleotide of SEQ ID NO: 2, as used herein, comprise any alteration in the sequence of polynucleotides encoding HPSK including deletions, insertions, and point mutations that may be detected using hybridization assays. Included within this definition is the detection of alterations to the genomic DNA sequence which encodes HPSK (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding HPSK (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind HPSK polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human prostate-specific kallikrein, (HPSK), the polynucleotides encoding HPSK, and the use of these compositions for the diagnosis, prevention, or treatment of prostate disorders including cancer.

Nucleic acids encoding the human HPSK of the present invention were first identified in Incyte Clone 1818001 from the prostate tissue cDNA library (PROSNOT20) through a computer-generated search for amino acid sequence alignments. A consensus sequence, SEQ ID NO:2, was derived from the following overlapping and/or extended nucleic acid sequences: Incyte Clones 1818001 (PROSNOT20), 786353 (PROSNOT05), 837074 (PROSNOT07), 1327152 (LPARNOT02), and 1682515 (PROSNOT15).

Figure 4:
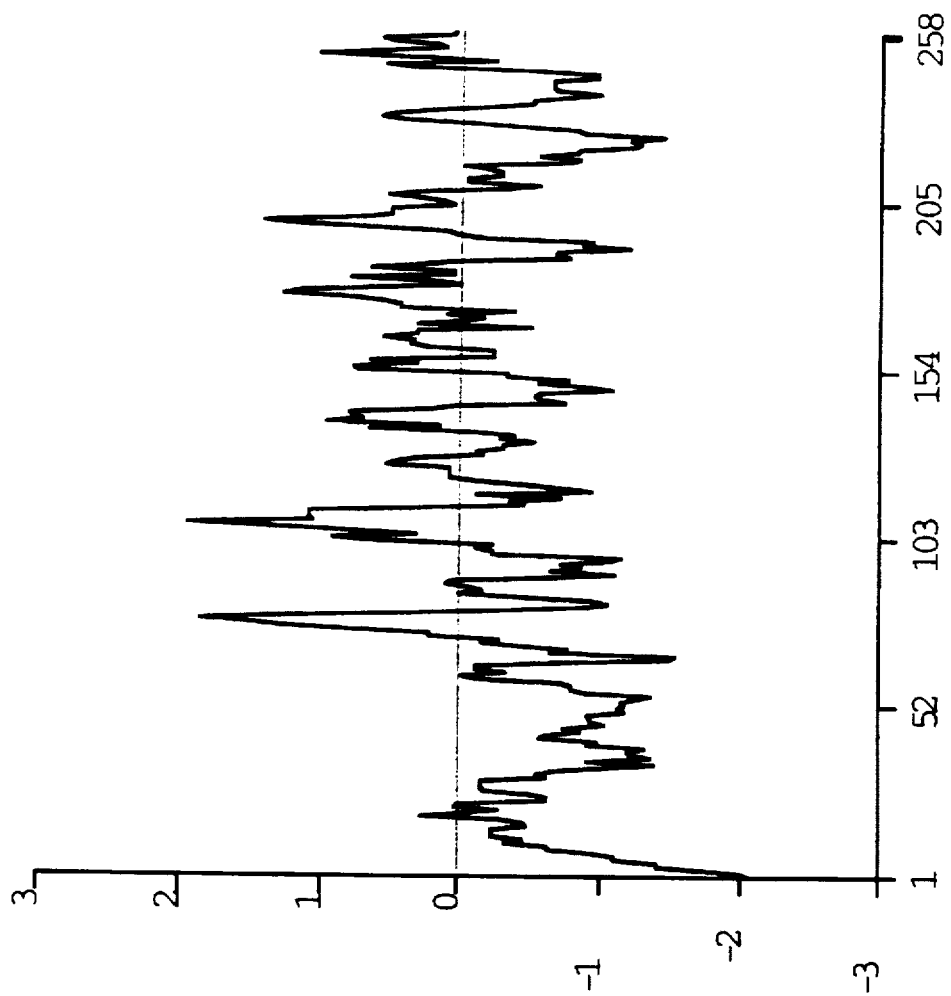
FIG. 4 shows the hydrophobicity plot for baboon KLK1, SEQ ID NO:3.

In one embodiment, the invention encompasses the novel human prostate-specific kallikrein, a polypeptide comprising the amino acid sequence of SEQ ID NO:1, as shown in FIG. 1. HPSK is 248 amino acids in length and has a potential N-glycosylation site at amino acid residue 163. HPSK has chemical and structural homology with baboon KLK1 (GI 871814; SEQ ID NO:3), human KLK1 (GI 186651; SEQ ID NO:4), and human PSA (GI 190553; SEQ ID NO:5). In particular, HPSK and baboon KLK1 share 56% identity. HPSK's amino terminal 24 amino acids are hydrophilic and closely resemble signal sequences important for kallikrein secretion (FIGS. 2, 3, and 4). HPSK sequence contains conserved residues critical for serine protease activity, $H_{65}$, $D_{110}$, and $S_{201}$ (FIG. 2). Amino acid residue $D_{195}$ is likely to confer on HPSK chymotrypsinogen-like activity. HPSK amino acid sequence includes 10 conserved cysteine residues (residues 31, 50, 66, 142, 161, 172, 186, 197, 207, and 222; FIG. 2). In all the kallikreins mentioned above these cysteines are structurally important, forming 5 disulfide bonds. As illustrated by FIGS. 3 and 4, HPSK and baboon KLK1 have rather similar hydrophobicity plots. Northern analysis reveals the expression pattern of this sequence in various libraries (FIG. 5). In addition, HPSK was found to be expressed in salivary gland tissue from a patient with cancer of the salivary gland. Of the 15 tissues in which HPSK is expressed, all but two are from the prostate gland and all but one are from cancer patients.

The invention also encompasses HPSK variants. A preferred HPSK variant is one having at least 80%, and more preferably 90%, amino acid sequence similarity to the HPSK amino acid sequence (SEQ ID NO:1). A most preferred HPSK variant is one having at least 95% amino acid sequence similarity to SEQ ID NO:1.

The invention also encompasses polynucleotides which encode HPSK. Accordingly, any nucleic acid sequence which encodes the amino acid sequence of HPSK can be used to generate recombinant molecules which express HPSK. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of nucleotide sequences encoding HPSK, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HPSK, and all such variations are to be considered as being specifically disclosed.

Although nucleotide sequences which encode HPSK and its variants are preferably capable of hybridizing to the nucleotide sequence of the naturally occurring HPSK under appropriately selected conditions of stringency, it may be advantageous to produce nucleotide sequences encoding HPSK or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HPSK and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HPSK and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HPSK or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152: 399–407) and Kimmel, A. R. (1987: Methods Enzymol. 152: 507–511), and may be used at a defined stringency.

Altered nucleic acid sequences encoding HPSK which are encompassed by the invention include deletions, insertions, or substitutions of different nucleotides resulting in a polynucleotide that encodes the same or a functionally equivalent HPSK. The encoded protein may also contain deletions, insertions, or substitutions of amino acid residues which produce a silent change and result in a functionally equivalent HPSK. Deliberate amino acid substitutions may be made on the basis of similarity in polarity, charge, solubility, hydrophobicity, hydrophilicity, and/or the amphipathic nature of the residues as long as the biological activity of HPSK is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding HPSK. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding HPSK may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2: 318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16: 8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19: 3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPSK, or fusion proteins or functional equivalents thereof, may be used in recombinant DNA molecules to direct expression of HPSK in appropriate host cells. Due to the inherent degeneracy of the genetic code, other DNA sequences which encode substantially the same or a functionally equivalent amino acid sequence may be produced and these sequences may be used to clone and express HPSK.

As will be understood by those of skill in the art, it may be advantageous to produce HPSK-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter HPSK encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding HPSK may be ligated to a heterologous sequence to encode a fusion protein. For example, to screen peptide libraries for inhibitors of HPSK activity, it may be useful to encode a chimeric HPSK protein that can be recognized by a commercially available antibody. A fusion protein may also be engineered to contain a cleavage site located between the HPSK encoding sequence and the heterologous protein sequence, so that HPSK may be cleaved and purified away from the heterologous moiety.

In another embodiment, sequences encoding HPSK may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HPSK, or a portion thereof. For example, peptide synthesis can be performed using various solid-phase techniques (Roberge, J. Y. et al. (1995) Science 269: 202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of HPSK, or any part thereof, may be altered during direct synthesis and/or combined using chemical methods with sequences from other proteins, or any part thereof, to produce a variant polypeptide.

In order to express a biologically active HPSK, the nucleotide sequences encoding HPSK or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HPSK and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HPSK. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HPSK, vectors based on SV40 or EBV may be used with an appropriate selectable marker.

In bacterial systems, a number of expression vectors may be selected depending upon the use intended for HPSK. For example, when large quantities of HPSK are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HPSK may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153: 516–544.

In cases where plant expression vectors are used, the expression of sequences encoding HPSK may be driven by any of a number of promoters. For example, viral promoters such as the 35S and 19S promoters of CaMV may be used alone or in combination with the omega leader sequence from TMV (Takamatsu, N. (1987) EMBO J. 6: 307–311). Alternatively, plant promoters such as the small subunit of RUBISCO or heat shock promoters may be used (Coruzzi, G. et al. (1984) EMBO J. 3: 1671–1680: Broglie, R. et al. (1984) Science 224: 838–843: and Winter, J. et al. (1991) Results Probl. Cell Differ. 17: 85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HPSK. For example, in one such system, *Autographa californica* nuclear polyhedrosis virus (AcNPV) is used as a vector to express foreign genes in *Spodoptera frugiperda* cells or in *Trichoplusia* larvae. The sequences encoding HPSK may be cloned into a non-essential region of the virus, such as the polyhedrin gene, and placed under control of the polyhedrin promoter. Successful insertion of HPSK will render the polyhedrin gene inactive and produce recombinant virus lacking coat protein. The recombinant viruses may then be used to infect, for example, *S. frugiperda* cells or Trichoplusia larvae in which HPSK may be expressed (Engelhard, E. K. et al. (1994) Proc. Nat. Acad. Sci. 91: 3224–3227).

In mammalian host cells, a number of viral-based expression systems may be utilized. In cases where an adenovirus is used as an expression vector, sequences encoding HPSK may be ligated into an adenovirus transcription/translation complex consisting of the late promoter and tripartite leader sequence. Insertion in a non-essential E1 or E3 region of the viral genome may be used to obtain a viable virus which is capable of expressing HPSK in infected host cells (Logan, J. and Shenk, T. (1984) Proc. Natl. Acad. Sci. 81: 3655–3659). In addition, transcription enhancers, such as the Rous sarcoma virus (RSV) enhancer, may be used to increase expression in mammalian host cells.

Specific initiation signals may also be used to achieve more efficient translation of sequences encoding HPSK. Such signals include the ATG initiation codon and adjacent sequences. In cases where sequences encoding HPSK, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20: 125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HPSK may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11: 223–32) and adenine phosphoribosyltransferase (Lowy, I. et al. (1980) Cell 22: 817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77: 3567–70); npt, which confers resistance to the aminoglycosides neomycin and G-418 (Colbere-Garapin, F. et al (1981) J. Mol. Biol. 150: 1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85: 8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121–131).

Although the presence/absence of marker gene expression suggests that the gene of interest is also present, its presence and expression may need to be confirmed. For example, if the sequence encoding HPSK is inserted within a marker gene sequence, recombinant cells containing sequences encoding HPSK can be identified by the absence of marker gene function. Alternatively, a marker gene can be placed in tandem with a sequence encoding HPSK under the control of a single promoter. Expression of the marker gene in response to induction or selection usually indicates expression of the tandem gene as well.

Alternatively, host cells which contain the nucleic acid sequence encoding HPSK and express HPSK may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HPSK can be detected by DNA-DNA or DNA-RNA hybridization or amplification using probes or portions or fragments of polynucleotides encoding HPSK. Nucleic acid amplification based assays involve the use of oligonucleotides or oligomers based on the sequences encoding HPSK to detect transformants containing DNA or RNA encoding HPSK. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HPSK, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HPSK is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPSK include oligolabeling, nick translation, end-labeling or PCR amplification using a labeled nucleotide. Alternatively, the sequences encoding HPSK, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HPSK may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HPSK may be designed to contain signal sequences which direct secretion of HPSK through a prokaryotic or eukaryotic cell membrane. Other recombinant constructions may be used to join sequences encoding HPSK to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HPSK may be used to facilitate purification. One such expression vector provides for expression of a fusion protein containing HPSK and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying HPSK from the fusion protein. A discussion of vectors which contain fusion proteins is provided in Kroll, D. J. et al. (1993; DNA Cell Biol. 12: 441–453).

In addition to recombinant production, fragments of HPSK may be produced by direct peptide synthesis using solid-phase techniques Merrifield J. (1963) J. Am. Chem. Soc. 85: 2149–2154). Protein synthesis may be performed using manual techniques or by automation. Automated synthesis may be achieved, for example, using Applied Biosystems 431A Peptide Synthesizer (Perkin Elmer). Various fragments of HPSK may be chemically synthesized separately and combined using chemical methods to produce the full length molecule.

THERAPEUTICS

In other embodiments of the invention, HPSK or fragments thereof may be used for therapeutic purposes.

Based on the chemical and structural homology among HPSK (SEQ ID NO:1), baboon and human KLK1 and northern analysis (FIG. 5) which shows that 13 of the 14 libraries containing HPSK transcripts are from prostate tissue, HPSK is believe to function in the prostate gland. Of the 13 prostate tissue libraries, 12 were from patients with prostate cancer. HPSK expression was additionally found in only two cDNA libraries, both from cancer patients, and therefore HPSK expression may be linked to tumorigenesis.

In one embodiment, vectors expressing antisense, antagonists or inhibitors of the protein may be used to suppress the excessive proliferation of prostate cells. Blocking HPSK expression or activity in the prostate may alter molecular pathway within cancerous cells and thus trigger programmed cell death. This therapeutic method can be used for the treatment of prostate cancer and benign prostate hyperplasia.

In another embodiment, other inhibitors which block or modulate the effect of HPSK may be used in those situations where such inhibition is therapeutically desirable. Such inhibitors may be produced using methods which are generally known in the art, and include particularly the use of purified HPSK to produce antibodies or to screen libraries of pharmaceutical agents for those which specifically bind HPSK. For example, in one aspect, antibodies which are specific for HPSK may be used directly as an antagonist, or indirectly as a targeting or delivery mechanism for bringing a pharmaceutical agent to cells or tissue which express HPSK.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HPSK or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HPSK have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HPSK amino acids may be fused with those of another protein such as keyhole limpet hemocyanin and antibody produced against the chimeric molecule.

Monoclonal antibodies to HPSK may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256: 495–497: Kozbor, D. et al. (1985) J. Immunol. Methods 81: 31–42; Cote, R. J. et al. (1983) Proc. Natl. Acad. Sci. 80: 2026–2030; Cole, S. P. et al. (1984) Mol. Cell Biol. 62: 109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81: 6851–6855; Neuberger, M. S. et al. (1984) Nature 312: 604–608; Takeda, S. et al. (1985) Nature 314: 452–454). Alternatively, techniques described for the production of single chain antibodies may be adapted, using methods known in the art, to produce HPSK-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88: 11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349: 293–299).

Antibody fragments which contain specific binding sites for HPSK may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254: 1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPSK and its specific antibody. A two-site, monoclonal-based immunoassay utilizing monoclonal antibodies reactive to two non-interfering HPSK epitopes is preferred, but a competitive binding assay may also be employed (Maddox, supra).

In another embodiment of the invention, the polynucleotides encoding HPSK, or any fragment thereof, or antisense molecules, may be used for therapeutic purposes. In one aspect, antisense to the polynucleotide encoding HPSK may be used in situations in which it would be desirable to block the transcription of the mRNA. In particular, cells may be transformed with sequences complementary to polynucleotides encoding HPSK. Thus, antisense molecules may be used to modulate HPSK activity, or to achieve regulation of gene function. Such technology is now well known in the art, and sense or antisense oligomers or larger fragments, can be designed from various locations along the coding or control regions of sequences encoding HPSK.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding HPSK. These techniques are described both in Sambrook et al. (supra) and in Ausubel et al. (supra).

Genes encoding HPSK can be turned off by transforming a cell or tissue with expression vectors which express high levels of a polynucleotide or fragment thereof which encodes HPSK. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HPSK, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HPSK.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HPSK. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HPSK, antibodies to HPSK, mimetics, agonists, antagonists, or inhibitors of HPSK. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HPSK, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HPSK or fragments thereof, antibodies of HPSK, agonists, antagonists or inhibitors of HPSK, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HPSK may be used for the diagnosis of conditions or diseases characterized by expression of HPSK, or in assays to monitor patients being treated with HPSK, agonists, antagonists or inhibitors. The antibodies useful for diagnostic purposes may be prepared in the same manner as those described above for therapeutics. Diagnostic assays for HPSK include methods which utilize the antibody and a label to detect HPSK in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HPSK are known in the art and provide a basis for diagnosing altered or abnormal levels of HPSK expression. Normal or standard values for HPSK expression are established by combining body fluids or cell extracts taken from normal mammalian subjects, preferably human, with antibody to HPSK under conditions suitable for complex formation. The amount of standard complex formation may be quantified by various methods, but preferably by photometric, means. Quantities of HPSK expressed in subject, control and disease, samples from biopsied tissues are compared with the standard values. Deviation between standard and subject values establishes the parameters for diagnosing disease.

In another embodiment of the invention, the polynucleotides encoding HPSK may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HPSK may be correlated with disease. The diagnostic assay may be used to distinguish between absence, presence, and excess expression of HPSK, and to monitor regulation of HPSK levels during therapeutic intervention.

In one aspect, hybridization with PCR probes which are capable of detecting polynucleotide sequences, including genomic sequences, encoding HPSK or closely related molecules, may be used to identify nucleic acid sequences which encode HPSK. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HPSK, alleles, or related sequences.

Probes may also be used for the detection of related sequences, and should preferably contain at least 50% of the nucleotides from any of the HPSK encoding sequences. The hybridization probes of the subject invention may be DNA or RNA and derived from the nucleotide sequence of SEQ ID NO:2 or from genomic sequence including promoter, enhancer elements, and introns of the naturally occurring HPSK.

Means for producing specific hybridization probes for DNAs encoding HPSK include the cloning of nucleic acid sequences encoding HPSK or HPSK derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HPSK may be used for the diagnosis of conditions or diseases which are associated with expression of HPSK. Examples of such conditions or diseases include, but are not limited to, prostatic carcinoma and benign prostate hyperplasia. Polynucleotide sequences encoding HPSK may also be used to monitor the progress of patients receiving treatment for prostatic carcinoma or benign prostatic hyperplasia. The polynucleotide sequences encoding HPSK may be used in Southern or northern analysis, dot blot, or other membrane-based technologies; in PCR technologies; or in dip stick, pin, ELISA or chip assays utilizing fluids or tissues from patient biopsies to detect altered HPSK expression. Such qualitative or quantitative methods are well known in the art.

In a particular aspect, the nucleotide sequences encoding HPSK may be useful in assays that detect activation or induction of various cancers, particularly those mentioned above. The nucleotide sequences encoding HPSK may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HPSK in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HPSK, a normal or standard profile for expression is established. This may be accomplished by combining body fluids or cell extracts taken from normal subjects, either animal or human, with a sequence, or a fragment thereof, which encodes HPSK, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HPSK may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HPSK include radiolabeling or biotinylating nucleotides, coamplification of a control nucleic acid, and standard curves onto which the experimental results are interpolated (Melby, P. C. wet al. (1993) J. Immunol. Methods, 159: 235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode HPSK may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7: 127–134, and Trask, B. J. (1991) Trends Genet. 7: 149–154.

FISH (as described in Verma et al. (1988) *Human Chromosomes: A Manual of Basic Techniques*. Pergamon Press, New York, N.Y.) may be correlated with other physical chromosome mapping techniques and genetic map data. Examples of genetic map data can be found in the 1994 Genome Issue of Science (265: 1981f). Correlation between the location of the gene encoding HPSK on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HPSK, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HPSK and the agent being tested, may be measured.

Another technique for drug screening which may be used provides for high throughput screening of compounds having suitable binding affinity to the protein of interest as described in published PCT application WO84/03564. In this method, as applied to HPSK large numbers of different small test compounds are synthesized on a solid substrate, such as plastic pins or some other surface. The test compounds are reacted with HPSK, or fragments thereof, and washed. Bound HPSK is then detected by methods well known in the art. Purified HPSK can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPSK specifically compete with a test compound for binding HPSK. In this manner, the antibodies can be used to detect the presence of any peptide which shares one or more antigenic determinants with HPSK.

In additional embodiments, the nucleotide sequences which encode HPSK may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I PROSNOT20 cDNA Library Construction

The PROSNOT20 cDNA library was constructed from prostate tissue, obtained from a 65-year-old Caucasian male (specimen #0223A&B; Mayo Clinic, Rochester, Minn.) during a radical prostatectomy. The patient presented with elevated prostate-specific antigen and was diagnosed as having a malignant neoplasm of the prostate. The pathology of the tumor indicated that the predominant mass involving the right anterior prostate peripherally was an adenocarcinoma (Gleason grade 2+2). Multiple microscopic foci were identified in the left and right sides of the prostate but did involve the capsule. Perineural invasion was present. Multiple pelvic lymph nodes were negative for tumor. There is no patient family history available, and the patient was taking no medication.

The frozen tissue was homogenized and lysed using a Brinkmann Homogenizer Polytron PT-3000 (Brinkmann Instruments, Westbury, N.J.) in guanidinium isothiocyanate solution. The lysates were centrifuged over a 5.7M CsCl cushion using an Beckman SW28 rotor in a Beckman L8-70M Ultracentrifuge (Beckman Instruments, Fullerton, Calif.) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen Oligotex kit (QIAGEN, Inc., Chatsworth, Calif.) and used to construct the cDNA libraries.

The mRNAs were handled according to the recommended protocols in the SuperScript Plasmid System for cDNA Synthesis and Plasmid Cloning (Cat. #18248-013, Gibco/BRL). The commercial plasmid pSPORT 1 (Gibco/BRL) was digested with EcoR I restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, E. coli strain JM 109. An intermediate plasmid produced by the bacteria failed to digest with EcoR I confirming the desired loss of the EcoRI restriction site.

This intermediate plasmid (pSPORT 1-ΔRI) was then digested with Hind III restriction enzyme (New England Biolabs) and the overhang was filled in with Klenow and dNTPs. A 10-mer linker of sequence 5' . . . CGGAATTCCG . . . 3' was phosphorylated and ligated onto the blunt ends. The product of the ligation reaction was digested with EcoR I and self-ligated. Following transformation into JM109 host cells, plasmids were isolated and screened for the digestibility with EcoR I but not with Hind III. A single colony which met this criteria was designated pINCY 1. The plasmid produced by this colony was sequenced and found to contain several copies of the 10-mer linker. These extra linkers did not present a problem as they were eliminated when the vector was prepared for cloning.

The plasmid was tested for its ability to incorporate cDNAs from a library prepared using Not I and EcoR I restriction enzymes. Several clones were sequenced and a single clone containing an insert of approximately 0.8 kb was selected to prepare a large quantity of the plasmid for library production. After digestion with Not I and EcoR I, the plasmid and the cDNA insert were isolated on an agarose gel and the vector was purified on a QIAQuick™ (QIAGEN) column for use in library construction.

cDNAs were fractionated on a Sepharose CL4B column (Cat. #275105-01, Pharmacia), and those cDNAs exceeding 400 bp were ligated into pSport I. The plasmid pSport I was subsequently transformed into DH5a™ competent cells (Cat. #18258-012, Gibco/BRL).

The RNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. 275105, Pharmacia), and those cDNAs exceeding 400 bp were ligated into pSport I. The plasmid pSport I was subsequently transformed into DH5a™ competent cells (Cat. #18258-012, Gibco/BRL).

II. Isolation and Sequencing of cDNA Clones

Plasmid DNA was released from the cells and purified using the REAL Prep 96 Plasmid Kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™, Gaithersburg, Md.) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94: 441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

Most of the sequences disclosed herein were sequenced according to standard ABI protocols, using ABI kits (Cat. Nos. 79345, 79339, 79340, 79357, 79355). The solution volumes were used at 0.25×–1.0× concentrations. Some of the sequences disclosed herein were sequenced using different solutions and dyes which, unless otherwise noted, came from Amersham Life Science (Cleveland, Ohio).

First, stock solutions were prepared with HPLC water. The following solutions were each mixed by vortexing for 2 min: 1) Tris-EDTA (TE) Buffer was prepared by adding 49 ml water to 1 ml 50×Tris-EDTA concentrate, and 2) 10% Reaction Buffer was prepared by adding 45 ml water to 5 ml Concentrated Thermo Sequenase (TS) Reaction Buffer.

Second, 0.2 μM energy transfer (ET) primers were prepared in the following manner. Each primer tube was centrifuged prior to opening to assure that all primer powder was on the bottom of the tube. After each solubilization step, the mixture was vortexed for 2 min and then centrifuged for about 10 sec in a table-top centrifuge. 1 ml of 1×TE was added to each primer powder; adenine and cytosine dissolved primers (5-carboxyrhodamine-6G (R6G) and 6-carboxyfluorescein (FAM), respectively), were diluted with 9 ml 1×TE. Guanine and thymine dyes (N,N,N',N''-tetramethyl-6-carboxyrhodamine (TAM) and 6-carboxy-X-rhodamine (ROX), respectively) were diluted with 19 ml 1×TE.

Next, the sequencing reaction ready mix was prepared as follows: 1) nucleotides A and C (8 ml of each) were added to 6 ml ET primer and 18 ml TS reaction buffer; and 2) nucleotides G and T (8 ml of each) were added to 6 ml ET primer and 18 ml TS reaction buffer.

After vortexing for 2 min and centrifuging for 20 sec, the resulting solution was divided into tubes in volumes of 8 ml per tube in order to make 1×(A,C) and 2×(G,T) solutions.

Prior to thermal cycling, each nucleotide was individually mixed with DNA template in the following proportions:

| Reagent | A(μL) | C(μL) | G(μL) | T(μL) |
| --- | --- | --- | --- | --- |
| Reaction ready premix | 2 | 2 | 4 | 4 |
| DNA template | 1 | 1 | 2 | 2 |
| Total Volume | 3 | 3 | 6 | 6 |

These solutions undergo the usual thermal cycling:

1. Rapid thermal ramp to 94° C. (94° C. for 20 sec)*
2. Rapid thermal ramp to 50° C. (50° C. for 40 sec)*
3. Rapid thermal ramp to 68° C. (68° C. for 60 sec)*

* Steps 1, 2, and 3 were repeated for 15 cycles

4. Rapid thermal ramp to 94° C. (94° C. for 20 sec)**
5. Rapid thermal ramp to 68° C. (68° C. for 60 sec)**

** Steps 4 and 5 were repeated for 15 cycles

6. Rapid thermal ramp to 4° C. and hold until ready to combine.

After thermal cycling, the A, C, G, and T reactions with each DNA template were combined. Then, 50 μL 100% ethanol was added and the solution was spun at 4° C. for 30 min. The supernatant was decanted and the pellet was rinsed with 100 μL 70% ethanol. After being spun for 15 min the supernatant was discarded and the pellet was dried for 15 min under vacuum. The DNA sample was dissolved in 3 μL of formamide/50 mM EDTA. The resulting samples were loaded on wells in volumes of 2 μL per well for sequencing in ABI sequencers.

III. Homology Searching of cDNA Clones and Their Deduced Proteins

After the reading frame was determined, the nucleotide sequences of the Sequence Listing as well as the amino acid sequences deduced from them were used as query sequences against databases such as GenBank, SwissProt, BLOCKS, and Pima II. These databases, which contain previously identified and annotated sequences, were searched for regions of homology (similarity) using BLAST, which stands for Basic Local Alignment Search Tool (Altschul S. F. (1993) J. Mol. Evol. 36: 290–300; Altschul, S. F. et al. (1990) J. Mol. Biol. 215: 403–10).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, *Protein Engineering* 5: 35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach, as detailed in Karlin et al. (supra) and incorporated herein by reference, searched for matches between a query sequence and a database sequence. BLAST evaluated the statistical significance of any matches found, and reported only those matches hat satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology. The relevant database for a particular match were reported as Glxxx±p (where xxx is pri; rod; etc.; and if present, p=peptide. The product score is calculated as follows: the % nucleotide or amino acid identity [between the query and reference sequences] in BLAST is multiplied by the % maximum possible BLAST score [based on the lengths of query and reference sequences] and then divided by 100. Where an Incyte Clone was homologous to several sequences, up to five matches were provided with their relevant scores. In an analogy to the hybridization procedures used in the laboratory, the electronic stringency for an exact match was set at 70, and the conservative lower limit for an exact match was set at approximately 40 (with 1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HPSK occurs. Abundance and percent abundance are also reported. Abundance directly reflects the number of times a particular transcript is represented in a cDNA library, and percent abundance is abundance divided by the total number of sequences examined in the cDNA library.

V Extension of HPSK-Encoding Polynucleotides to Full Length or to Recover Regulatory Sequences Full length HPSK-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the HPSK-encoding sequence, or any part thereof, is used to inhibit in vivo or in vitro expression of naturally occurring HPSK. Although use of antisense oligonucleotides, comprising about 20 base-pairs, is specifically described, essentially the same procedure is used with larger cDNA fragments. An oligonucleotide based on the coding sequences of HPSK, as shown in FIG. 1, is used to inhibit expression of naturally occurring HPSK. The complementary oligonucleotide is designed from the most unique 5' sequence as shown in FIG. 1 and used either to inhibit transcription by preventing promoter binding to the upstream nontranslated sequence or translation of an HPSK-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIG. 1.

VIII Expression of HPSK

Expression of HPSK is accomplished by subcloning the cDNAs into appropriate vectors and transforming the vectors into host cells. In this case, the cloning vector, pSport, previously used for the generation of the cDNA library is used to express HPSK in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HPSK into the bacterial growth media which can be used directly in the following assay for activity.

IX Demonstration of HPSK Activity

HPSK's proteolytic activity can be determined by methods described by Christernsson A. et al. (1990, Eur. J. Biochem. 194: 755–763). Substrates for proteolytic cleavage are found in human semen. Human seminal plasma is collected and coagulated semen is washed free of soluble components. HPSK is incubated with coagulated semen in a buffer consisting of 50 mmol/l TRIS-HCl pH 7.8, with 0.1 mol/l NaCl. Reactions are performed at 37° C. After incubation periods of different durations (from 0 to 30 minutes) the samples are analysed by SDS/PAGE. The resulting pattern of peptide fragments is compared and quantitated using a control sample in which HPSK was not added.

X Production of HPSK Specific Antibodies

HPSK that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HPSK Using Specific Antibodies

Naturally occurring or recombinant HPSK is substantially purified by immunoaffinity chromatography using antibodies specific for HPSK. An immunoaffinity column is constructed by covalently coupling HPSK antibody to an activated chromatographic resin, such as CnBr-activated Sepharose (Pharmacia & Upjohn). After the coupling, the resin is blocked and washed according to the manufacturers instructions.

Media containing HPSK is passed over the immunoaffinity column, and the column is washed under conditions that allow the preferential absorbance of HPSK (e.g., high ionic strength buffers in the presence of detergent). The column is eluted under conditions that disrupt antibody/HPSK binding (eg, a buffer of pH 2–3 or a high concentration of a chaotrope, such as urea or thiocyanate ion), and HPSK is collected.

XII Identification of Molecules Which Interact with HPSK

HPSK or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HPSK, washed and any wells with labeled HPSK complex are assayed. Data obtained using different concentrations of HPSK are used to calculate values for the number, affinity, and association of HPSK with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding a prostate-specific kallikrein comprising the amino acid sequence of SEQ ID NO:1.

2. An isolated and purified polynucleotide sequence which hybridizes under stringent wash conditions of 0.1× saline sodium citrate and 0.5% sodium dodecyl sulfate to the polynucleotide sequence of claim 1.

3. A hybridization probe comprising the polynucleotide sequence of claim 1.

4. An isolated and purified polynucleotide sequence comprising SEQ ID NO:2.

5. A polynucleotide sequence which is complementary to SEQ ID NO:2.

6. A hybridization probe comprising the polynucleotide sequence of claim 5.

7. An expression vector containing the polynucleotide sequence of claim 1.

8. A host cell containing the vector of claim 7.

9. A method for producing a polypeptide comprising the amino acid sequence of SEQ ID NO:1 the method comprising the steps of:

a) culturing the host cell of claim 8 under conditions suitable for the expression of the polypeptide; and b) recovering the polypeptide from the host cell culture.

10. A method for detection of polynucleotides encoding the prostate-specific kallikrein of claim 1 in a biological sample comprising the steps of:

a) hybridizing a polynucleotide consisting of SEQ ID NO:2 to nucleic acid material of a biological sample, thereby forming a hybridization complex; and b) detecting said hybridization complex, wherein the presence of said complex correlates with the presence of a polynucleotide encoding prostate-specific kallikrein in said biological sample.

11. The method of claim 10 wherein before hybridization, the nucleic acid material of the biological sample is amplified by the polymerase chain reaction.

* * * * *